United States Patent
Moriya et al.

(10) Patent No.: US 8,344,732 B2
(45) Date of Patent: Jan. 1, 2013

(54) MEASURING SYSTEM

(75) Inventors: Masahiko Moriya, Musashino (JP);
Naoki Maeda, Musashino (JP);
Toshimitsu Uemura, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 316 days.

(21) Appl. No.: 12/696,869

(22) Filed: Jan. 29, 2010

(65) Prior Publication Data
US 2010/0194397 A1    Aug. 5, 2010

(30) Foreign Application Priority Data

Jan. 30, 2009    (JP) .................................. 2009-019574

(51) Int. Cl.
*G01N 27/416* (2006.01)
*H02J 7/00* (2006.01)
*H01M 10/48* (2006.01)

(52) U.S. Cl. ........ 324/427; 320/131; 320/135; 324/426; 324/433; 429/90; 429/91; 429/92

(58) Field of Classification Search .................. 324/427; 320/135, 131
See application file for complete search history.

(56) References Cited

U.S. PATENT DOCUMENTS

| | | | | |
|---|---|---|---|---|
| 5,254,928 A | * | 10/1993 | Young et al. | 320/125 |
| 6,377,030 B1 | * | 4/2002 | Asao et al. | 320/161 |
| 6,990,422 B2 | * | 1/2006 | Laletin et al. | 702/109 |
| 7,667,942 B2 | * | 2/2010 | Boling | 361/103 |
| 8,164,307 B2 | * | 4/2012 | Cargonja et al. | 320/132 |
| 2005/0127879 A1 | * | 6/2005 | Sato et al. | 320/134 |
| 2007/0138998 A1 | * | 6/2007 | Togashi et al. | 320/104 |
| 2008/0143297 A1 | * | 6/2008 | Lafleur et al. | 320/136 |
| 2008/0203995 A1 | * | 8/2008 | Carrier et al. | 323/351 |

FOREIGN PATENT DOCUMENTS

| | | |
|---|---|---|
| JP | 03203523 A | 9/1991 |
| JP | 5-63837 A | 3/1993 |
| JP | 5-176091 A | 7/1993 |
| JP | 5-323000 A | 12/1993 |
| JP | 2001086658 A | 3/2001 |

OTHER PUBLICATIONS

Japanese Office Action corresponding to Japanese Patent Application No. JP 2009-019574, dated Jul. 11, 2011.

* cited by examiner

*Primary Examiner* — Drew A Dunn
*Assistant Examiner* — Nathaniel Pelton
(74) *Attorney, Agent, or Firm* — Sughrue Mion, PLLC

(57) ABSTRACT

There is provided a measuring system capable of rendering a power source voltage of an internal circuit higher than a drivable voltage of the internal circuit by removing or reducing a chloride film with greater certainty, thereby enabling operation, and initial activation of the internal circuit to be normally executed, or preventing the internal circuit from running away. The measuring system comprises a thionyl chloride based primary cell, a cell voltage measurement unit, and an internal circuit provided with state-transition controller wherein in the case of transition of the internal circuit to a state thereof, having a discharge current larger than the discharge current in the present state thereof, the transition is made according to results of comparison of a voltage measured by the cell voltage measurement unit with a threshold on the basis of a discharge current in a state before, or after the transition of the internal circuit.

5 Claims, 6 Drawing Sheets

FIG. 2

| Respective units | Operation modes | Consumed current symbols | Examples of consumed current values |
|---|---|---|---|
| Control operation unit | Low-speed mode | Iml | 1.2mA |
| | High-speed mode | Imh | 2.2mA |
| | Boot mode | Irb | 30mA |
| | Reset mode | Irr | 1mA |
| Communication unit | Standby mode | Iri | 0.005mA |
| | Communication mode | Irc | 18mA |
| First circuit block | On-mode for First connector | Ilcd | 0.1mA |
| Second circuit block | On-mode for Second connector | Isns | 1.6mA |
| First-predetermined current discharge unit | Discharge mode | Il1 | 1mA |
| Second-predetermined current discharge unit | Discharge mode | Il2 | 10mA |

FIG. 3

| State | Control operation unit | Communication unit | First circuit block | Second circuit block | First-Predetermined current discharge unit | Second-Predetermined current discharge unit | Discharge currnt |
|---|---|---|---|---|---|---|---|
| 1 | Low-speed mode | Reset mode | Off-mode for First connector | Off-mode for Second connector | Non-discharge mode | Non-discharge mode | Id1=Iml+Irr |
| 1a | | Reset mode | Off-mode for First connector | Off-mode for Second connector | Discharge mode | Non-discharge mode | Id1a=Iml+Irr+Il1 |
| 2 | High-speed mode | Reset mode | On-mode for First connector | Off-mode for Second connector | Non-discharge mode | Non-discharge mode | Id2=Imh+Irr+Ilcd |
| 2a | | | On-mode for First connector | Off-mode for Second connector | Discharge mode | Non-discharge mode | Id2a=Imh+Irr+Ilcd+Il1 |
| 2b | | | On-mode for First connector | Off-mode for Second connector | Non-discharge mode | Discharge mode | Id2b=Imh+Irr+Ilcd+Il2 |
| 3 | High-speed mode | Boot mode | On-mode for First connector | Off-mode for Second connector | Non-discharge mode | Non-discharge mode | Id3=Imh+Irb+Ilcd |
| 4 | High-speed mode | Standby mode | On-mode for First connector | On-mode for Second connector | Non-discharge mode | Non-discharge mode | Id4=Imh+Iri+Ilcd+Isns |
| 4a | | | On-mode for First connector | On-mode for Second connector | Discharge mode | Non-discharge mode | Id4a=Imh+Iri+Ilcd+Isns+Il1 |
| 4b | | | On-mode for First connector | On-mode for Second connector | Non-discharge mode | Discharge mode | Id4b=Imh+Iri+Ilcd+Isns+Il2 |
| 5 | High-speed mode | Communication mode | On-mode for First connector | On-mode for Second connector | Non-discharge mode | Non-discharge mode | Id5=Imh+Irc+Ilcd+Isns |

MEASURING SYSTEM

FIELD OF THE INVENTION

The invention relates to a measuring system, and in particular, to a measuring system for controlling a discharge current of a thionyl chloride based primary cell by controlling a state transition of an internal circuit, thereby removing or reducing a chloride film formed on the surface of an anode.

BACKGROUND OF THE INVENTION

In process control carried out at a chemical plant and so forth, use is made of a measuring system driven by, for example, a built-in thionyl chloride based primary cell for measurement of process parameters (pressure, temperature, flow rate, and so forth) of a fluid under test. The measuring system is described hereinafter with reference to a block diagram of FIG. 6.

In FIG. 6, a measuring system 10 comprises a thionyl chloride based primary cell 1, and an internal circuit 9. The internal circuit 9 is comprised of a constant voltage circuit unit 2, a connection controller 3, a control operation unit 4, a communication unit 5 for executing radio communication or wire communication, a first connector 6a, a second connector 6b, a first circuit block 7a, a second circuit block 7b, and a cell voltage measurement unit 8.

An anode (an output) of the thionyl chloride based primary cell 1 is connected to an input of the constant voltage circuit unit 2 as well as the cell voltage measurement unit 8 while a cathode thereof is connected to a common voltage GD.

The constant voltage circuit unit 2 converts an output voltage of the thionyl chloride based primary cell 1 into a predetermined voltage (for example, 3.3 V) to be subsequently outputted. An output of the constant voltage circuit unit 2 is connected to the connection controller 3, the control operation unit 4, the communication unit 5, the first connector 6a, and the second connector 6b, respectively, as a power source thereof, respectively, the output of the constant voltage circuit unit 2 being further connected to the first circuit block 7a via the first connector 6a, and to the second circuit block 7b via the second connector 6b, as a power source thereof, respectively.

The first circuit block 7a is provided with a display unit made up of liquid crystals and so forth, for displaying measured values, and the second circuit block 7b is provided with a sensor for detecting the process parameters of the fluid under test, and so forth.

The cell voltage measurement unit 8 takes measurements on the output voltage of the thionyl chloride based primary cell 1, and an output of the cell voltage measurement unit 8 is connected to the connection controller 3. The communication unit 5 receives a communication signal EXT from outside, and an output thereof is connected to the connection controller 3.

The control operation unit 4 is connected to the first circuit block 7a, the second circuit block 7b, and the connection controller 3, thereby transmitting and receiving data such as measured values, and so forth, and a control signal. Further, the control operation unit 4 receives a process signal detected by the sensor of the second circuit block 7b, and calculates the measured value (a process value) on the basis of the process signal, outputting the measured value to the first circuit block 7a to be thereby displayed.

With the thionyl chloride based primary cell 1, and the internal circuit 9, constituted as described above, the internal circuit 9 is driven upon receiving supply of a discharge current from the thionyl chloride based primary cell 1, the discharge current serving as a power source current.

Now, in the case of the communication unit 5 carrying out radio communication via an antenna AT, the thionyl chloride based primary cell 1 large in power capacity, and small in self-discharge is employed as the power source of the measuring system 10 provided with a radio communication function. Further, for the thionyl chloride based primary cell 1 wherein thionyl chloride is used as solvent, use is made of, for example, a lithium thionyl chloride primary cell.

The thionyl chloride based primary cell 1 has an advantage in that a chloride film is formed on the surface of an anode in view of its properties, and according to its preservation state, and so forth, thereby preventing self-discharge. On the other hand, internal resistance will increase due to the chloride film formed therein. In this case, if there occurs an increase in the discharge current, this will cause an increase in voltage drop due to internal resistance, thereby lowering an output voltage.

With the measuring system 10 provided with the radio communication function, employing the thionyl chloride based primary cell 1 as the power source of the system, when measurement or radio communication is not executed, the measuring system 10 is in a standby state where a consumed current (power source current) is small in order to check a decrease in the power capacity of the cell while the measuring system 10 is in a normal operation state where the consumed current (the power source current) is large when the measurement or the radio communication is executed.

In this connection, since the consumed current in the standby state is very small in value, and if the standby state lasts for a long duration, a chloride film is formed, continuing growth. In the case of an increase in internal resistance, due to growth of the chloride film, if the measuring system 10 shifts to the normal operation state, thereby causing the consumed current to increase, this will raise a possibility that the output voltage of the thionyl chloride based primary cell 1 will drop to thereby cause stoppage in operation of the internal circuit 9, or the internal circuit 9 will occasionally run away.

Furthermore, if use is made of the thionyl chloride based primary cell 1 that has been unused as yet, and preserved over a long term, thereby causing growth of the chloride film, and resulting in a large internal resistance, there can be cases where initial activation of the internal circuit 9 cannot be effected because of a drop in the output voltage of the thionyl chloride based primary cell 1 at the time of the initial activation.

Accordingly, in order to normally effect the operation, and the initial activation of the internal circuit 9, or to prevent the internal circuit 9 from running away, the discharge current is controlled as follows.

In a first control of the discharge current, the discharge current is increased in stages. Such an operation is described hereinafter.

In FIG. 6, first, the control operation unit 4 such as a processor and so forth is in the standby state before the communication unit 5 receives the communication signal EXT via the antenna AT. In the standby state, the consumed current of the control operation unit 4 is small in value, so that the discharge current of the thionyl chloride based primary cell 1 is also small in value (step A).

Subsequently, upon receiving the communication signal EXT, the communication unit 5 outputs an interrupt signal to the connection controller 3. The connection controller 3 outputs a state-control signal to the control operation unit 4, and the control operation unit 4 receives the state-control signal, whereupon the control operation unit 4 shifts from the standby state to the operation state.

In the operation state, as the consumed current of the control operation unit 4 increases, so does the discharge current as well. As a result of an increase in the discharge current, the voltage drop due to the internal resistance will increase, so that the output voltage of the thionyl chloride based primary cell 1 will abruptly drop (step B).

While the output voltage of the thionyl chloride based primary cell 1 abruptly drops, the chloride film is removed, or reduced due to an increase in the discharge current, thereby reducing the internal resistance, whereupon the output voltage is gradually restored. Accordingly, the connection controller 3 monitors the output voltage of the thionyl chloride based primary cell 1, measured by the cell voltage measurement unit 8, and waits until the output voltage is restored to a voltage sufficient to enable the internal circuit 9 to be driven.

After restoration of the voltage, the connection controller 3 outputs a connection control signal to the first connector 6a, and upon the first connector 6a receiving the connection control signal, the first connector 6a connects input/output thereof.

By so doing, the first circuit block 7a receives supply of the power source current from the constant voltage circuit unit 2 via the first connector 6a, so that the discharge current will increase. As a result of an increase in the discharge current, the output voltage of the thionyl chloride based primary cell 1 undergoes an abrupt drop (step C).

Then, the connection controller 3 waits until the output voltage of the thionyl chloride based primary cell 1 is restored. After restoration of the voltage, the connection controller 3 outputs a connection control signal to the second connector 6b, and upon the second connector 6b receiving the connection control signal, the second connector 6b connects input/output thereof.

By so doing, the second circuit block 7b receives supply of the power source current from the constant voltage circuit unit 2 via the second connector 6b, so that the discharge current will increase. As a result of an increase in the discharge current, the output voltage of the thionyl chloride based primary cell 1 undergoes an abrupt drop, and thereafter, the output voltage is restored (step D).

Thus, the internal circuit 9 has a plurality of states differing in the discharge current from the step to the step. And current is supplied in stages to the respective units {including the respective blocks (the same applies hereinafter)} of the internal circuit 9 to cause the discharge current to increase, thereby normally executing the operation and the initial activation of the internal circuit 9, or preventing the internal circuit 9 from running away. Similar control of the discharge current is described in Patent Document 1.

In a second control of the discharge current, a time length for causing the discharge current to flow is computed on the basis of an average consumed current of the internal circuit 9, and the chloride film is activated by causing the discharge current to flow during the time length, thereby normally executing the operation and the initial activation of the internal circuit 9, or preventing the internal circuit 9 from running away. Similar control of the discharge current is described in Patent Document 2 (in Patent Document 2, the time length for causing the discharge current to flow is defined as refresh time).

Further, in Patent Document 3, there is described a technology capable of checking whether a voltage drop detection signal of the thionyl chloride based primary cell 1 is attributable to insufficient removal of the chloride film, or to a drop in the cell voltage, thereby sending out accurate information on the drop in the cell voltage.

[Preceding Technical Literature]
[Patent Document] JP 1993-176091A
[Patent Document] JP 1993-63837 A
[Patent Document] JP 1993-323000 A

SUMMARY OF THE INVENTION

However, if the discharge current is small in magnitude, it is not possible to remove or reduce the chloride film that has already grown. For this reason, it is not possible to remove or reduce the chloride film in the first control of the discharge current even when the discharge current is increased if a discharge current flow rate itself is small, so that the output voltage of the thionyl chloride based primary cell 1 is not restored after undergoing an abrupt drop.

Because the output voltage is not restored, the connection controller 3 remains in the standby state, so that the operation is unable to proceed to the next step, failing to normally effect the operation, and the initial activation of the internal circuit 9. Further, because the output voltage remains at a low level, failing to reach a voltage for enabling the internal circuit 9 to be driven, there can be times when the internal circuit 9 runs away.

Furthermore, a thickness of the chloride film is affected by ambient temperature, time during which the thionyl chloride based primary cell 1 is in use, preservation time during which the thionyl chloride based primary cell 1 is out of use, and so forth. For this reason, in the second control of the discharge current, even if the discharge current is caused to flow for the time length (the refresh time) computed on the basis of the average consumed current of the internal circuit 9, there can be times when the chloride film cannot be removed, or reduced.

In such a case, since the output voltage of the thionyl chloride based primary cell 1 drops, failing to reach the voltage for enabling the internal circuit 9 to be driven, there can be times when it is not possible to normally effect the operation, and the initial activation of the internal circuit 9, or the internal circuit 9 runs away.

It is therefore an object of the invention to provide a measuring system capable of rendering a power source voltage of an internal circuit higher than a drivable voltage of the internal circuit by removing or reducing a chloride film with greater certainty, thereby enabling operation, and initial activation of the internal circuit to be normally executed, or preventing the internal circuit from running away.

To that end, in accordance with one aspect of the present invention, there is provided a measuring system comprising a thionyl chloride based primary cell, a cell voltage measurement unit for taking measurements on an output voltage of the thionyl chloride based primary cell, and an internal circuit for receiving supply of a discharge current from the thionyl chloride based primary cell, having a plurality of states differing from each other in magnitude of the discharge current, the internal circuit comprising a state-transition controller wherein in the case of transition of the internal circuit to a state thereof, having a discharge current larger than the discharge current in the present state thereof, the transition is made according to results of comparison of a voltage measured by the cell voltage measurement unit with a threshold on the basis of a discharge current in a state before, or after the transition of the internal circuit.

The internal circuit may comprise a predetermined current discharge unit for causing flow of a predetermined discharge current.

The state-transition controller may change a value of the predetermined discharge current of the predetermined current discharge unit.

If the state of the internal circuit, for flow of the predetermined discharge current by the action of the predetermined current discharge unit, is repeated a plurality of times, the state-transition controller may prevent the internal circuit from making transition to another state of the internal circuit, where discharge current in another state is larger in value than discharge current in the present state of the internal circuit.

If the voltage measured by the cell voltage measurement unit is smaller in value than the smallest threshold among the thresholds, the state-transition controller may prevent the internal circuit from making transition to another state of the internal circuit, where discharge current in another state is larger in value than discharge current in the present state of the internal circuit.

The threshold may be a value based on a ratio of the discharge current in a state of the internal circuit, prior to transition, to the discharge current in a state of the internal circuit, after the transition, and based on a predetermined output voltage of the thionyl chloride based primary cell at no-load.

With the present invention, in the case of the internal circuit making transition to another state of the internal circuit, where discharge current is larger in value than discharge current in the present state of the internal circuit, the state-transition controller causes the state of the internal circuit to undergo transition according to results of comparison of the voltage measured by the cell voltage measurement unit with the threshold on the basis of the discharge current in the state before, or after the transition of the internal circuit, so that a chloride film is removed or reduced with greater certainty, the power source voltage of the internal circuit is rendered higher than a drivable voltage of the internal circuit, thereby enabling operation, and initial activation of the internal circuit to be normally executed, or preventing the internal circuit from running away.

BRIEF DESCRIPTION OF THE DRAWINGS

FIG. 2 is a table showing respective units of an internal circuit, operation modes of respective units, consumed current symbols in respective operation modes, and examples of respective consumed current values;

FIG. 3 is a table showing a plurality of states of the internal circuit, the respective operation modes of the respective units in the respective states, and examples of discharge currents in the respective states;

DETAILED DESCRIPTION OF THE PREFERRED EMBODIMENTS

[First Embodiment]

Figure 1:
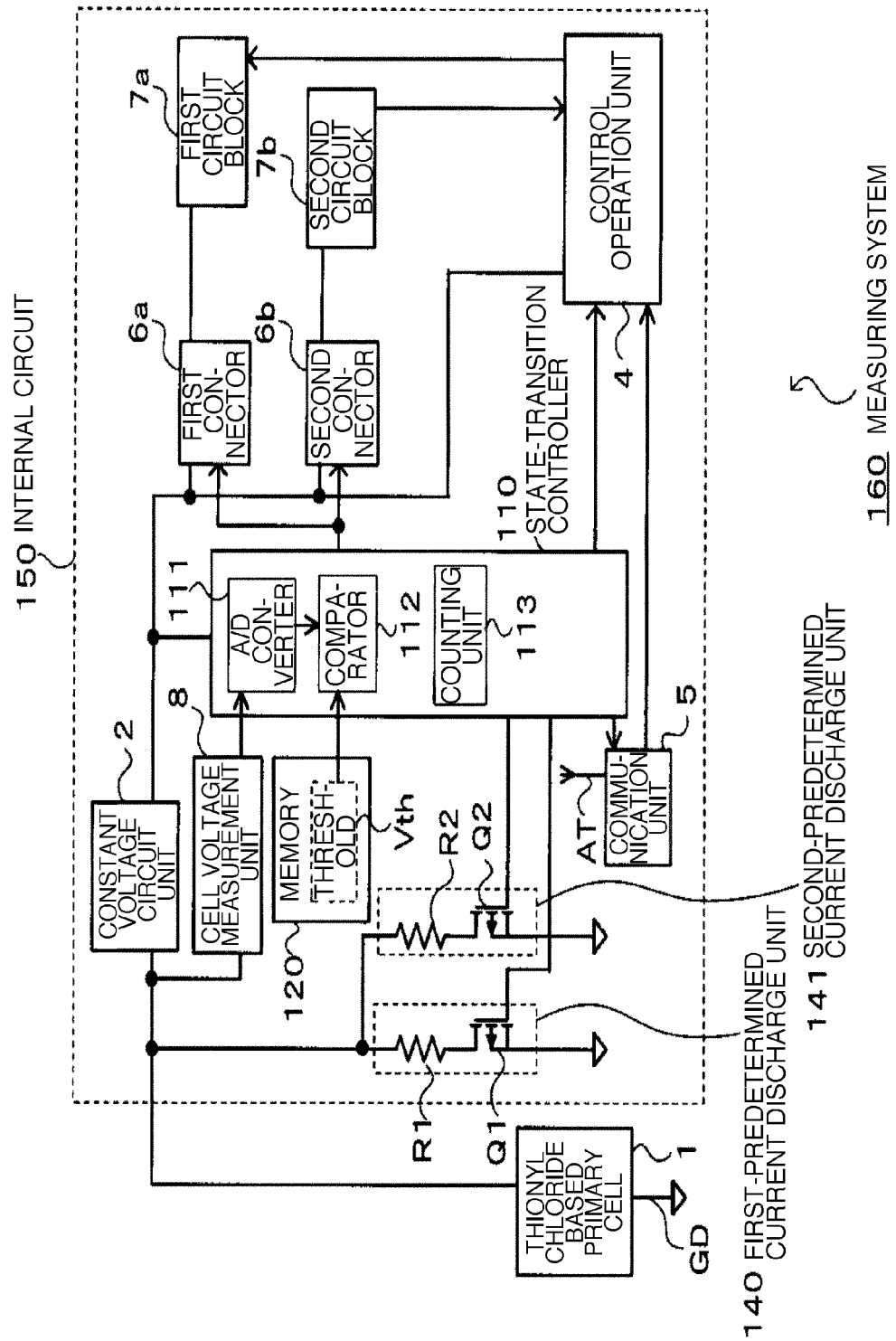
FIG. 1 is a block diagram of an embodiment of a measuring system according to the invention.

A first embodiment of a measuring system according to the invention is described with reference to FIG. 1. FIG. 1 is a block diagram of a measuring system 160 according to the invention.

Figure 6:
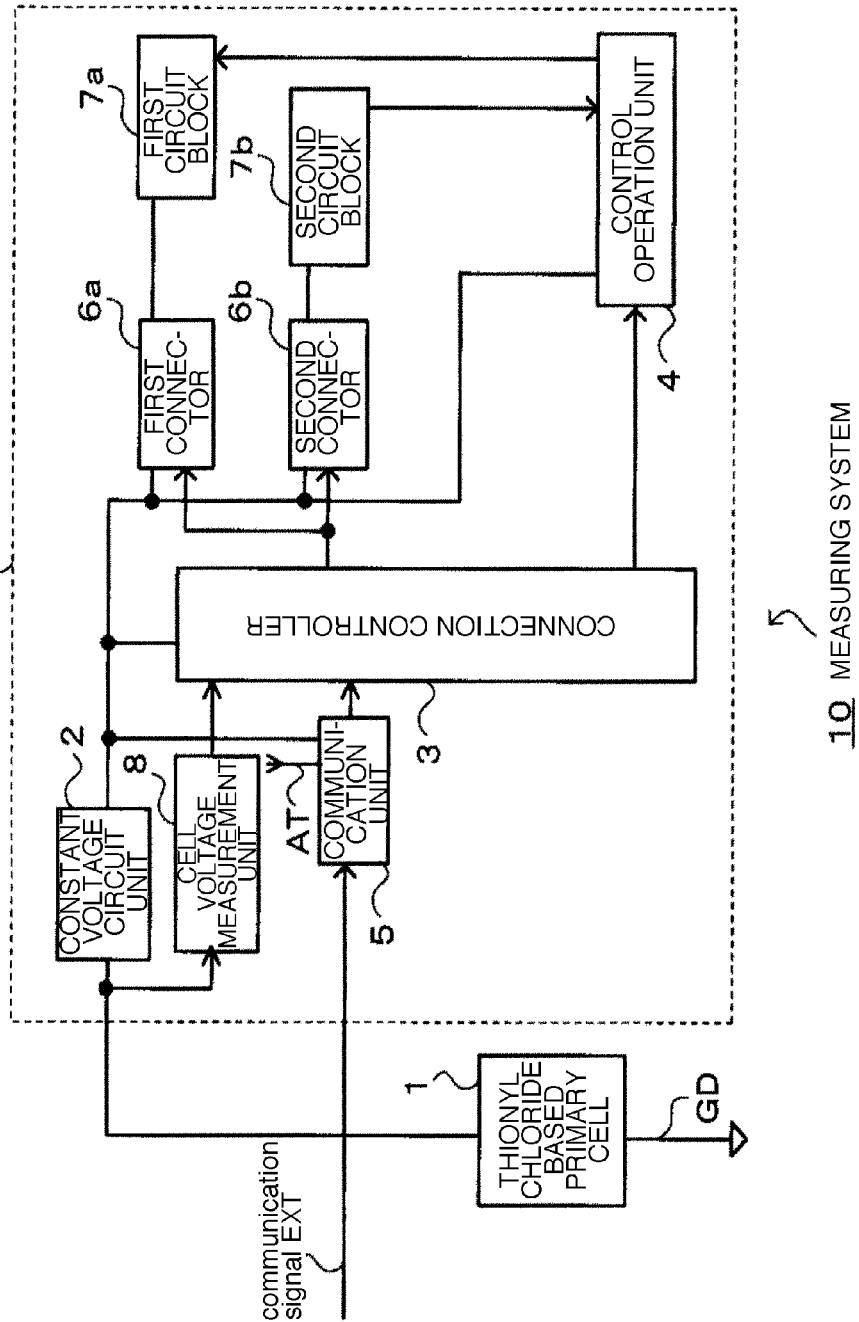
FIG. 6 is a block diagram of an example of a measuring system, shown under BACKGROUND OF THE INVENTION.

In FIG. 1, the measuring system 160 has a configuration of the measuring system 10 shown in FIG. 6, without the connection controller 3, and in addition to the configuration, an internal circuit 150 further comprises a state-transition controller 110, a memory 120 storing thresholds Vth, a first-predetermined current discharge unit 140, and a second-predetermined current discharge unit 141.

One of features of the measuring system 160 according to the invention lies in the state-transition controller 110 for causing a state of the internal circuit 150 to undergo transition according to results of comparison of an output voltage of a thionyl chloride based primary cell 1, measured by a cell voltage measurement unit 8, with the threshold Vth, and discharge current is controlled according to such state-transition. Further, a value of the threshold Vth is another of the features, and explanation centering around those features is described hereinafter. Furthermore, in FIG. 1, constituents identical to those of the measuring system 10 shown in FIG. 6 are denoted by like reference numerals, omitting description thereof.

The state-transition controller 110 is comprised of an A/D converter 111, a comparator 112, and a counting unit 113. The A/D converter 111 receives a measured output voltage (hereinafter referred to as a measured cell voltage) of a thionyl chloride based primary cell 1 from the cell voltage measurement unit 8. The comparator 112 receives a digitally converted measured cell voltage from the A/D converter 111 while receiving the threshold Vth from the memory 120.

The state-transition controller 110 causes the state of the internal circuit 150 to undergo transition according to the results of the comparison by the comparator 112. An operation for transition is described in detail later on in the present description.

Further, the counting unit 113 is provided with a timer or a counter, measuring an elapsed time length for the internal circuit 150 in a predetermined state.

The first-predetermined current discharge unit 140 is provided with a resistor R1 and a transistor (field effect transistor) Q1.

The resistor R1 has one end connected to an anode (output) of the thionyl chloride based primary cell 1, and the other end connected to a drain of the transistor Q1. The transistor Q1 has a gate connected to the state-transition controller 110, and a source connected to a common voltage GD of the circuit.

Now, operation of the measuring system 160 is described hereinafter. First, respective operation modes of the internal circuit 150 are described with reference to FIG. 2. FIG. 2 is a table showing respective units of the internal circuit 150, operation modes of the respective units, consumed current symbols in the respective operation modes, and examples of respective consumed current values. Herein, the respective consumed currents represent a power source current for driving the respective units, the power source current being fed by a discharge current from the thionyl chloride based primary cell 1.

In FIG. 2, a control operation unit 4 has two modes including a low-speed mode for executing control operation at a low speed, and a high-speed mode for executing the control operation at a high speed.

In the low-speed mode, a consumed current symbol is Iml, and an example of a consumed current value is 1.2 mA. In the high-speed mode, a consumed current symbol is Imh, and an example of the consumed current value is 2.2 mA.

A communication unit 5 shown in the following line in the table has four modes including a boot mode for executing activation processing of a built-in communication module, a reset mode for resetting the communication module, a standby mode for waiting for communication, and a communication mode for executing communication.

In the boot mode, the consumed current symbol is Irb, and an example of the consumed current value is 30 mA. In the reset mode, the consumed current symbol is Irr, and an example of the consumed current value is 1 mA. In the standby mode, the consumed current symbol is Iri, and the example of the consumed current value is 0.005 mA. In the communication mode, the consumed current symbol is Irc, and an example of the consumed current value is 18 mA.

A first circuit block 7a shown in the following line in the table has an off-mode (not shown), and an on-mode for a first connector 6a.

In the off-mode, input/output of the first connector 6a is not connected to the first circuit block 7a, so that the first circuit block 7a does not receive supply of a power source current from a constant voltage circuit unit 2.

On the other hand, in the on-mode, the input/output of the first connector 6a is connected to the first circuit block 7a, so that the first circuit block 7a receives supply of the power source current from the constant voltage circuit unit 2.

In the off-mode, no current flows to the first circuit block 7a, so that the consumed current value is 0 mA. On the other hand, in the on-mode, the consumed current symbol is Ilcd, and an example of the consumed current value is 0.1 mA.

Similarly, a second circuit block 7b shown in the following line in the table has an off-mode (not shown), and an on-mode with respect to a second connector 6b.

In the off-mode, input/output of the second connector 6b is not connected to the second circuit block 7b, so that the second circuit block 7b does not receive supply of the power source current from the constant voltage circuit unit 2.

On the other hand, in the on-mode, the input/output of the second connector 6b is connected to the second circuit block 7b, so that the second circuit block 7b receives supply of the power source current from the constant voltage circuit unit 2.

In the off-mode, no current flows to the second circuit block 7b, so that the consumed current value is 0 mA. On the other hand, in the on-mode, the consumed current symbol is Isns, and an example of the consumed current value is 1.6 mA.

The first-predetermined current discharge unit 140 shown in the following line in the table has a non-discharge mode (not shown), and a discharge mode.

In the non-discharge mode, electrical continuity does not exist between the source and the drain of the transistor Q1 by the agency of a gate control signal from the state-transition controller 110, so that the discharge current from the thionyl chloride based primary cell 1 does not flow to the resistor R1 and the transistor Q1.

On the other hand, in the discharge mode, electrical continuity exists between the source and the drain of the transistor Q1 by the agency of the gate control signal from the state-transition controller 110, so that the discharge current from the thionyl chloride based primary cell 1 flows to the resistor R1 and the transistor Q1.

In the non-discharge mode, since no current flows, the consumed current value is 0 mA. On the other hand, in the discharge mode, the consumed current symbol is Il1, and an example of the consumed current value is 1 mA.

Similarly, the second-predetermined current discharge unit 141 shown in the following line in the table has a non-discharge mode (not shown), and a discharge mode.

In the non-discharge mode, electrical continuity does not exist between the source and the drain of the transistor Q2 by the agency of the gate control signal from the state-transition controller 110, so that the discharge current from the thionyl chloride based primary cell 1 does not flow to a resistor R2, and a transistor Q2.

On the other hand, in the discharge mode, electrical continuity exists between the source and the drain of the transistor Q2 by the agency of the gate control signal from the state-transition controller 110, so that the discharge current from the thionyl chloride based primary cell 1 flows to the resistor R2, and the transistor Q2.

In the non-discharge mode, since no current flows, the consumed current value is 0 mA. On the other hand, in the discharge mode, the consumed current symbol is Il2, and an example of the consumed current value is 10 mA.

Furthermore, the discharge modes of the first-predetermined current discharge unit 140, and the second-predetermined current discharge unit 141, respectively, refer to a mode adopted for removal of the chloride film, unrelated to measurement processing by the measuring system 160.

Accordingly, for obtaining a predetermined discharge current value in the discharge mode, it need only be sufficient to set a current necessary for removal of the chloride film.

As shown in FIG. 2, the respective units have the respective operation modes. And if the measuring system 160 undergoes initial activation, the internal circuit 150 operates while undergoing transition among a plurality of states, resulting from various combinations of the respective operation modes of the respective units. The plurality of the states of the internal circuit 150 are described hereinafter before describing such a transition operation.

The plurality of the states of the internal circuit 150, the respective operation modes of the respective units in the respective states, and discharge currents in the respective states are described with reference to a table of FIG. 3. Those discharge currents each being the sum of the consumed currents of the respective units in the respective operation modes, those discharge currents differ in magnitude from each other.

In FIG. 3, the plurality of the states of the internal circuit 150 are ten states, that is, states 1, 1a, 2, 2a, 2b, 3, 4, 4a, 4b, and 5. The respective operation modes of the respective units in the respective states, and the discharge currents in the respective states will be as follows.

The state 1 is described by way of example. In the state 1, the control operation unit 4 is in the low-speed mode (the consumed current at Iml), the communication unit 5 is in the reset mode (the consumed current at Irr), the first circuit block 7a is in the off-mode with respect to the first connector 6a, the second circuit block 7b is in the off-mode with respect to the second connector 6b, and the first-predetermined current discharge unit 140 in the non-discharge mode is combined with the second-predetermined current discharge unit 141 in the non-discharge mode, a discharge current being at Id1 {Id1=Iml+Irr (=2.2 mA) (example)}.

Similarly, in FIG. 3, there are described the plurality of the states, resulting from the various combinations of the respective operation modes of the respective units, and the discharge currents in the respective states with respect to each of the states 1a to 5.

Figure 4:
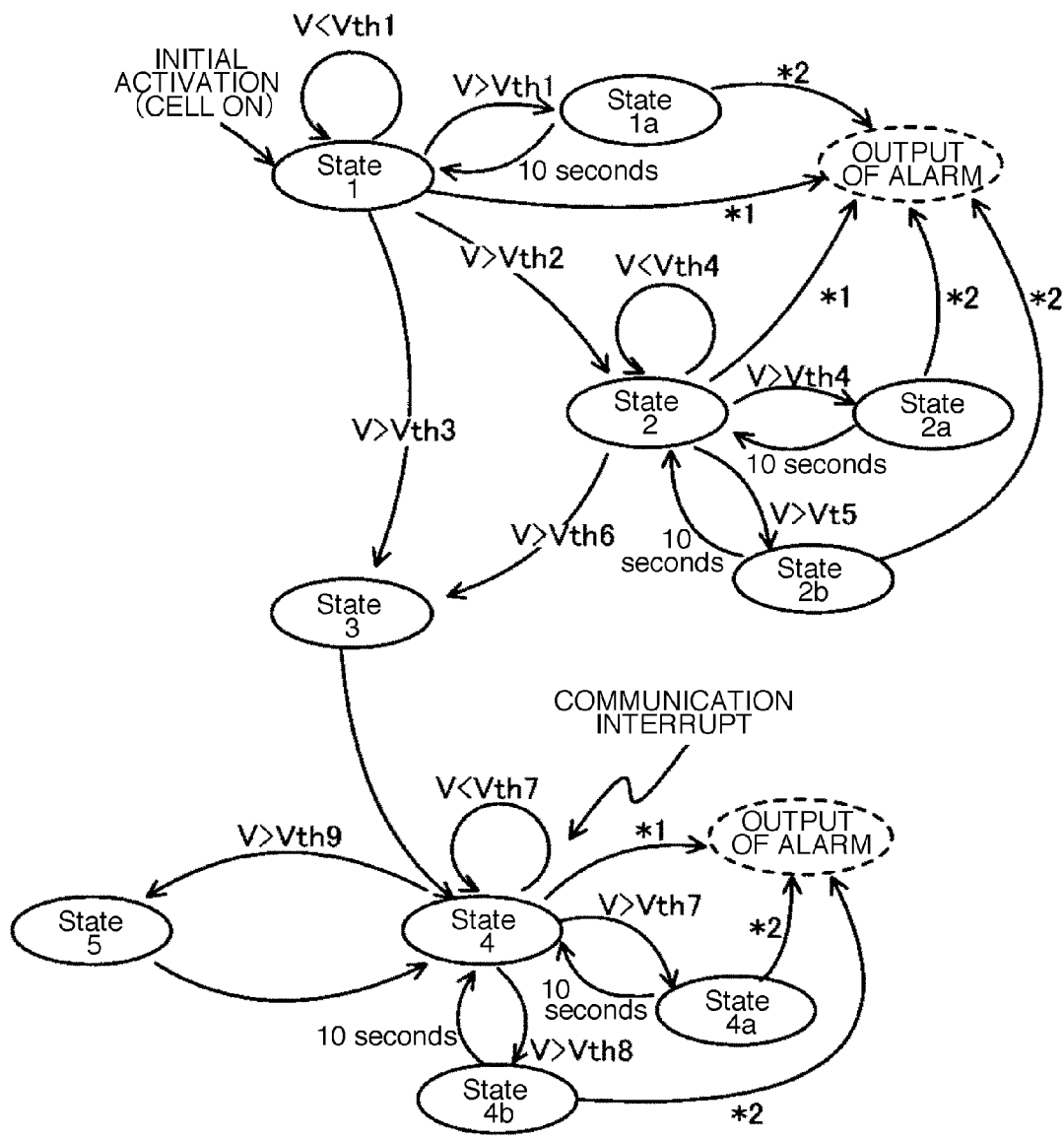
FIG. 4 is a state-transition view showing an operation of a state-transition controller, for causing a state of the internal circuit to undergo transition.

Next, referring to FIG. 4, there is described hereinafter an operation of the state-transition controller 110, for causing the state of the internal circuit 150 to transition after the initial activation of the measuring system 160. FIG. 4 is a state-transition view showing the operation of the state-transition controller 110, for causing the state of the internal circuit 150 to undergo transition.

The state-transition controller 110 causes the state of the internal circuit 150 to undergo transition to a state having a discharge current larger than the discharge current in the present state according to the results of comparison of the measured cell voltage with a threshold Vth on the basis of a discharge current in a state before, or after the transition of the internal circuit 150.

Assuming that the measuring system 160 first undergoes the initial activation, and the internal circuit 150 is in the state 1, respective transition operations (the case of transition from the state 1 to the state 3, the case of transition from the state 1 to the state 2, the case of transition from the state 2 to the state 3, and the case of transition from the state 4 to the state 5) taking place thereafter are described hereinafter with reference to in FIG. 4.

<The Case of Transition from the State 1 to the State 3>

In the state 1, the A/D converter 111 converts the measured cell voltage received from the cell voltage measurement unit 8 into a digital signal. The comparator 112 receives the digital signal converted from the measured cell voltage from the A/D converter 111 while receiving the threshold Vth from the memory 120.

In this case, the threshold Vth is a threshold in the case of transition from the state 1 to the state 3, a symbol thereof being designated as Vth3.

The threshold Vth3 can be obtained from a ratio of the discharge current at Id1{=2.2 mA (example)} in the state 1, that is, a state prior to the transition (the present state) to the discharge current at Id3 {=32.3 mA (example)} in the state 3, that is, a state after the transition.

More specifically, assuming that an output voltage of the thionyl chloride based primary cell 1 at no-load is Ve (for example, 7.2V), and the lowest voltage capable of driving the internal circuit 150 is Vd (for example, 3V or less, hereinafter referred to as the lowest drive voltage), the threshold Vth3 is obtained by expression (1) as follows:

$$Vth3 = Ve - \frac{Id1}{Id3} \times (Ve - Vd) \quad (1)$$
$$= \left(1 - \frac{Id1}{Id3}\right) \times Ve + \frac{Id1}{Id3} \times Vd$$

The comparator 112 compares a measured cell voltage with the threshold Vth3, and if the measured cell voltage is larger, or higher than the threshold Vth3, the communication unit 5 is capable of booting, so that the state-transition controller 110 causes the state of the internal circuit 150 to undergo transition to the state 3.

Further, assuming that the discharge current in a state prior to transition is Inow, and the discharge current in a state after the transition is Inext, general expression for obtaining the threshold Vth is expression (2) as follows:

$$Vth = Ve - \frac{Inow}{Inxt} \times (Ve - Vd) \quad (2)$$
$$= \left(1 - \frac{Inow}{Inxt}\right) \times Ve + \frac{Inow}{Inxt} \times Vd$$

In the expression (2), the threshold Vth can be obtained by use of a ratio of the discharge current Inow in the state prior to the transition to the discharge current Inext in the state after the transition, larger than Inow. For this reason, in the case where the internal circuit 150 undergoes transition according to the results of comparison of the measured cell voltage with the threshold Vth of the expression (2), power source voltages of the respective units of the internal circuit 150, after the transition, will be higher than the lowest drive voltage Vd, so that the internal circuit 150 will normally undergo the initial activation, and the operation without running away.

Further, relationship in magnitude among the threshold Vth3, and thresholds to be described later on, namely, the thresholds 1, 2, 4 to 9, respectively, are expressed by expressions (3) to (5) as follows if a discharge current value is found by use of the examples of the consumed current values, in FIG. 2.

$$Vth1 < Vth2 < Vth3 \quad (3)$$

$$Vth4 < Vth5 < Vth6 \quad (4)$$

$$Vth7 < Vth8 < Vth9 \quad (5)$$

<The Case of Transition from the State 1 to the State 2>

In this case, the threshold Vth is a threshold in the case of transition from the state 1 to the state 2, a symbol thereof being designated as Vth2. The threshold Vth2 can be obtained from the expression (2) by use of the discharge current Id1 {=2.2 mA (example)} in the state 1, that is, the state prior to the transition, and the discharge current Id2 {=3.3 mA (example)} in the state 2, that is, a state after the transition.

The comparator 112 compares the measured cell voltage with the threshold Vth2, and if the measured cell voltage is larger, or higher than the threshold Vth2, and is smaller, or lower than the threshold Vth3, the communication unit 5 is not capable of booting, but the control operation unit 4 can be set to the high-speed mode while the first circuit block 7a is operable, enabling the first connector 6a to be set to the on-mode. Accordingly, the state-transition controller 110 can cause the internal circuit 150 to undergo transition to the state 2.

<The Case of Transition from the State 2 to the State 3>

In this case, the threshold Vth is a threshold in the case of transition from the state 2 to the state 3, a symbol thereof being designated as Vth6. The threshold Vth6 can be obtained from the expression (2) by use of the discharge current Id2 {=3.3 mA (example)} in the state 2, that is, a state prior to the transition, and the discharge current Id3 {=32.3 mA (example)} in the state 3, that is, a state after the transition.

The comparator 112 compares the measured cell voltage with the threshold Vth6, and if the measured cell voltage is larger, or higher than the threshold Vth6, the communication unit 5 is capable of booting, so that the state-transition controller 110 causes the state of the internal circuit 150 to undergo transition to the state 3.

Then, after transition to the state 3, the communication unit 5 executes activation processing of the built-in communication module (a boot mode) before transition to the state 4.

<The Case of Transition from the State 4 to the State 5>

In the state 4, the communication unit 5 stands by until a communication signal is received, thereby receiving a communication interrupt (a standby mode). In the case of a radio communication cycle being as long as several hours, there is a possibility that the chloride film will undergo growth in a period of time during which the internal circuit 150 remains in the state 4. The internal circuit 150, after receiving the communication interrupt, undergoes transition to the state 5, however, the internal circuit 150 executes a transition operation described hereunder to prevent an abnormal operation thereof, due to the chloride film that has grown.

In this case, the threshold Vth is a threshold in the case of transition from the state 4 to the state 5, a symbol thereof being designated as Vth9. The threshold Vth9 can be obtained from the expression (2) by use of the discharge current Id4 {=3.905 mA (example)} in the state 4, that is, a state prior to the transition, and the discharge current Id5 {=21.9 mA (example)} in the state 5, that is, a state after the transition.

The comparator 112 compares the measured cell voltage with the threshold Vth9, and if the measured cell voltage is larger, or higher than the threshold Vth9, the communication unit 5 is capable of communication, so that the state-transition controller 110 causes the state of the internal circuit 150 to undergo transition to the state 5. Upon completion of the communication, the communication unit 5 undergoes transition to the state 4, and stands by.

Thus, the state-transition controller 110 causes the state of the internal circuit 150 to undergo transition according to the results of comparison of the measured cell voltage with the threshold Vth expressed by the expression (2) to thereby remove or reduce the chloride film with greater certainty, so that the power source voltages of the respective units of the internal circuit 150, after the transition, will be higher than the lowest drive voltage Vd, and the state-transition controller 110 can normally execute he initial activation as well as the operation of the internal circuit 150, or prevent the internal circuit 150 from running away.

Further, the state-transition controller 110 can normally execute the initial activation as well as the operation of the internal circuit 150 without setting the first-predetermined current discharge unit 140 or the second-predetermined current discharge unit 141 to the discharge mode (more specifically, without setting the first-predetermined current discharge unit 140 or and the second-predetermined current discharge unit 141 to any of the states 1a, 2a, 2b, 4a, and 4b). Accordingly, the state-transition controller 110 can normally execute the initial activation as well as the operation of the internal circuit 150 without causing excess discharge current to flow, thereby realizing low power consumption.

Next, respective operations of the first-predetermined current discharge unit 140 or and the second-predetermined current discharge unit 141, for making transition to the states 1a, 2a, 2b, 4a, and 4b, for the discharge mode, (the case of transition from the state 1 to the state 1a, the case of transition from the state 2 to the state 2b, the case of transition from the state 2 to the state 2a, the case of transition from the state 4 to the state 4b, and the case of transition from the state 4 to the state 4a) are described hereinafter with reference to in FIG. 4.

<The Case of Transition from the State 1 to the State 1a>

In this case, the threshold Vth is a threshold in the case of transition from the state 1 to the state 1a, a symbol thereof being designated as Vth1. The threshold Vth1 can be obtained from the expression (2) by use of the discharge current Id1 {=2.2 mA (example)} in the state 1, that is, a state prior to the transition, and the discharge current Id1a {=3.2 mA (example)} in the state 1a, that is, a state after the transition.

The comparator 112 compares the measured cell voltage with the threshold Vth1, and if the measured cell voltage is larger, or higher than the threshold Vth1, and is smaller, or lower than the threshold Vth2, it is not possible to implement transition to the states 2, and 3. For this reason, the state-transition controller 110 causes the internal circuit 150 to undergo transition to the state 1a in order to effect forced transition in the discharge mode of the first-predetermined current discharge unit 140, thereby removing the chloride film.

<The Case of Transition from the State 2 to the State 2b>

In this case, the threshold Vth is a threshold in the case of transition from the state 2 to the state 2b, a symbol thereof being designated as Vth5. The threshold Vth5 can be obtained from the expression (2) by use of the discharge current Id2 {=3.3 mA (example)} in the state 2, that is, a state prior to the transition, and the discharge current Id2b {=13.3 mA (example)} in the state 2b, that is, a state after the transition.

The comparator 112 compares the measured cell voltage with the threshold Vth5, and if the measured cell voltage is larger, or higher than the threshold Vth5, and is smaller, or lower than the threshold Vth6, it is not possible to effect boot-processing of the communication unit 5, so that transition to the state 3 cannot be effected. For this reason, the state-transition controller 110 causes the internal circuit 150 to undergo transition to the state 2b in order to effect forced transition in the discharge mode of the second-predetermined current discharge unit 141, thereby removing the chloride film.

<The Case of Transition from the State 2 to the State 2a>

In this case, the threshold Vth is a threshold in the case of transition from the state 2 to the state 2a, a symbol thereof being designated as Vth4. The threshold Vth4 can be obtained from the expression (2) by use of the discharge current Id2 {=3.3 mA (example)} in the state 2, that is, the state prior to the transition, and the discharge current Id2a {=4.3 mA (example)} in the state 2a, that is, a state after the transition.

The comparator 112 compares the measured cell voltage with the threshold Vth4, and if the measured cell voltage is larger, or higher than the threshold Vth4, and is smaller, or lower than the threshold Vth5, it is not possible to effect boot-processing of the communication unit 5, so that transition to the state 3 cannot be effected. For this reason, the state-transition controller 110 causes the internal circuit 150 to undergo transition to the state 2a in order to effect forced transition in the discharge mode of the first-predetermined current discharge unit 140, thereby removing the chloride film.

<The Case of Transition from the State 4 to the State 4b>

In this case, the threshold Vth is a threshold in the case of transition from the state 4 to the state 4b, a symbol thereof being designated as Vth8. The threshold Vth8 can be obtained from the expression (2) by use of the discharge current Id4 {=3.905 mA (example)} in the state 4, that is, a state prior to the transition, and the discharge current Id4b {=13.905 mA (example)} in the state 4b, that is, a state after the transition.

The comparator 112 compares the measured cell voltage with the threshold Vth8, and if the measured cell voltage is larger, or higher than the threshold Vth8, and is smaller, or lower than the threshold Vth9, it is not possible to execute communication, so that transition to the state 5 cannot be effected. For this reason, the state-transition controller 110 causes the internal circuit 150 to undergo transition to the state 4b in order to effect forced transition in the discharge mode of the second-predetermined current discharge unit 141, thereby removing the chloride film.

<The Case of Transition from the State 4 to the State 4a>

In this case, the threshold Vth is a threshold in the case of transition from the state 4 to the state 4a, a symbol thereof being designated as Vth7. The threshold Vth7 can be obtained from the expression (2) by use of the discharge current Id4 {=3.905 mA (example)} in the state 4, that is, the state prior to the transition, and the discharge current Id4a {=4.905 mA (example)} in the state 4a, that is, a state after the transition.

The comparator 112 compares the measured cell voltage with the threshold Vth7, and if the measured cell voltage is larger in value, or higher than the threshold Vth7, and is smaller in value, or lower than the threshold Vth8, it is not possible to execute communication, so that transition to the state 5 cannot be effected. For this reason, the state-transition controller 110 causes the internal circuit 150 to undergo transition to the state 4a in order to effect forced transition in the discharge mode of the first-predetermined current discharge unit 140, thereby removing the chloride film.

Thus, if the state-transition controller 110 sets the first-predetermined current discharge unit 140 or the second-predetermined current discharge unit 141 to the discharge mode to thereby cause forced discharge, the chloride film is removed or reduced with greater certainty, and the power source voltages of the respective units of the internal circuit 150, after the transition, become higher than the lowest drive voltage Vd, so that the state-transition controller 110 can normally execute the initial activation as well as the operation of the internal circuit 150, or prevent the internal circuit 150 from running away.

In this connection, the first-predetermined current discharge unit 140, and the second-predetermined current discharge unit 141 may be combined with each other into one predetermined current discharge unit, and by so doing, circuit space and cost can be reduced. Further, the number of the predetermined current discharge unit may be increased, in which case, more delicate control of discharge current can be implemented, thereby removing or reducing the chloride film.

Further, if a predetermined value such as a manufacturer's specified value, and so forth is used for the output voltage Ve of the thionyl chloride based primary cell 1, at no-load, the threshold Vth is insusceptible to effects of variation in no-load output voltage Ve of a cell actually in use, due to individual difference.

More specifically, if the no-load output voltage Ve of the cell actually in use is smaller in value than the predetermined value, a drop in the measured cell voltage can be detected earlier, and if the no-load output voltage Ve of the cell actually in use is larger in value than the predetermined value, a drop in the measured cell voltage can be detected with sufficient lead time. In consequence, even if there occurs variation in the no-load output voltage Ve of a cell actually in use, due to individual difference, the state-transition controller 110 can normally execute the initial activation as well as the operation of the internal circuit 150, or prevent the internal circuit 150 from running away.

Next, there is described an operation for detecting insufficiency in power capacity of the thionyl chloride based primary cell 1, and so forth, with reference to FIG. 4.

In FIG. 4, with the elapse of predetermined time (for example, 10 seconds) according to measurement by the counting unit 113, after the transition of the internal circuit 150 to the state 1*a*, the state-transition controller 110 causes the internal circuit 150 to make transition to the state 1. The cell voltage measurement unit 8 takes measurements again, and if the measured cell voltage is larger in value, or higher than the threshold Vth1, and is smaller in value, or lower than the threshold Vth2, the state-transition controller 110 causes the internal circuit 150 to make transition to the state 1*a*.

If the transition between the state 1, and the state 1*a* is repeated several times (for example, three times), more specifically, if the state 1*a* of forced transition in the discharge mode of the first-predetermined current discharge unit 140 is repeated several times, there occurs insufficiency in power capacity of the thionyl chloride based primary cell 1, or the chloride film cannot be removed or reduced, so that there is a possibility that if the internal circuit 150 is left as it is, the power source voltages of the respective units of the internal circuit 150 becomes smaller in value than the lowest drive voltage Vd, and consequently, a normal operation of the internal circuit 150 cannot be executed, or the internal circuit 150 runs away.

In such a case, the state-transition controller 110 outputs an alarm via an alarm unit (not shown) such as a buzzer (sound) and a lamp (light), the communication unit 5, or the display unit of the first circuit block 7*a*, without causing the internal circuit 150 to make transition from the state 1*a* to another state (refer to an arrow*2 from the state 1*a* in FIG. 4).

Similarly, if the transition between the state 2*a*, and the state 2, or between the state 2*b*, and the state 2 is repeated several times (for example, three times), more specifically, if the state 2*a*, or 2*b* of forced transition in the discharge mode of the first-predetermined current discharge unit 140, or the second-predetermined current discharge unit 141, respectively, is repeated several times, the state-transition controller 110 outputs an alarm without causing the internal circuit 150 to make transition to another state (refer to an arrow*2 from the state 2*a*, 2*b*, in FIG. 4).

Similarly, if the transition between the state 4*a*, and the state 4, or between the state 4*b*, and the state 4 is repeated several times (for example, three times), more specifically, if the state 4*a*, or 4*b* of forced transition in the discharge mode of the first-predetermined current discharge unit 140, or the second-predetermined current discharge unit 141, respectively, is repeated several times, the state-transition controller 110 outputs an alarm without causing the internal circuit 150 to make transition to another state (refer to an arrow*2 from the state 4*a*, 4*b*, in FIG. 4).

Furthermore, with the execution of the following operation as well, an alarm can be similarly outputted by detecting insufficiency in power capacity of the thionyl chloride based primary cell 1, and so forth.

The smallest threshold among the thresholds in the expression (3) is Vth1. In the state 1, if the measured cell voltage is smaller in value, or lower than the threshold Vth1, and even with the elapse of predetermined time (for example, 30 seconds) according to measurement by the counting unit 113, the measured cell voltage is smaller in value, or lower than the threshold Vth1, there occurs insufficiency in power capacity of the thionyl chloride based primary cell 1, or the chloride film cannot be removed or reduced, so that there is a possibility that if the internal circuit 150 is left as it is, the power source voltages of the respective units of the internal circuit 150 become smaller in value than the lowest drive voltage Vd, and consequently, a normal operation of the internal circuit 150 cannot be executed, or the internal circuit 150 runs away.

In such a case, the state-transition controller 110 outputs an alarm via the alarm unit (not shown), the communication unit 5, or the display unit of the first circuit block 7*a*, without causing the internal circuit 150 to make transition from the state 1 to another state (refer to an arrow*1 from the state 1 in FIG. 4).

Similarly, the smallest threshold among the thresholds in the expression (4) is Vth4. In the state 2, if the measured cell voltage is smaller in value, or lower than the threshold Vth4, and even with the elapse of predetermined time (for example, 30 seconds) according to measurement by the counting unit 113, the measured cell voltage is smaller in value, or lower than the threshold Vth4, the state-transition controller 110 outputs an alarm without causing the internal circuit 150 to make transition to another state (refer to an arrow*1 from the state 2 in FIG. 4).

Similarly, the smallest threshold among the thresholds in the expression (5) is Vth7. In the state 4, if the measured cell voltage is smaller in value, or lower than the threshold Vth7, and even with the elapse of predetermined time (for example, 30 seconds) according to measurement by the counting unit 113, the measured cell voltage is smaller in value, or lower than the threshold Vth7, the state-transition controller 110 outputs an alarm without causing the internal circuit 150 to make transition to another state (refer to an arrow*1 from the state 4 in FIG. 4).

Thus, if a state of forced transition in the discharge mode of the first-predetermined current discharge unit 140*m* or the second-predetermined current discharge unit 141 is repeated several times, the state-transition controller 110 outputs an alarm without causing the internal circuit 150 to make transition to another state, thereby detecting in advance a possibility that a normal operation of the internal circuit 150 cannot be executed, or the internal circuit 150 runs away because of insufficiency in the power capacity, or a drop in the power source voltages of the respective units of the internal circuit 150, so that the state-transition controller 110 is able to report the possibility to outside, and to take countermeasures such as repair, replacement, and so forth prior to occurrence of a trouble.

[Second Embodiment]

Figure 5:
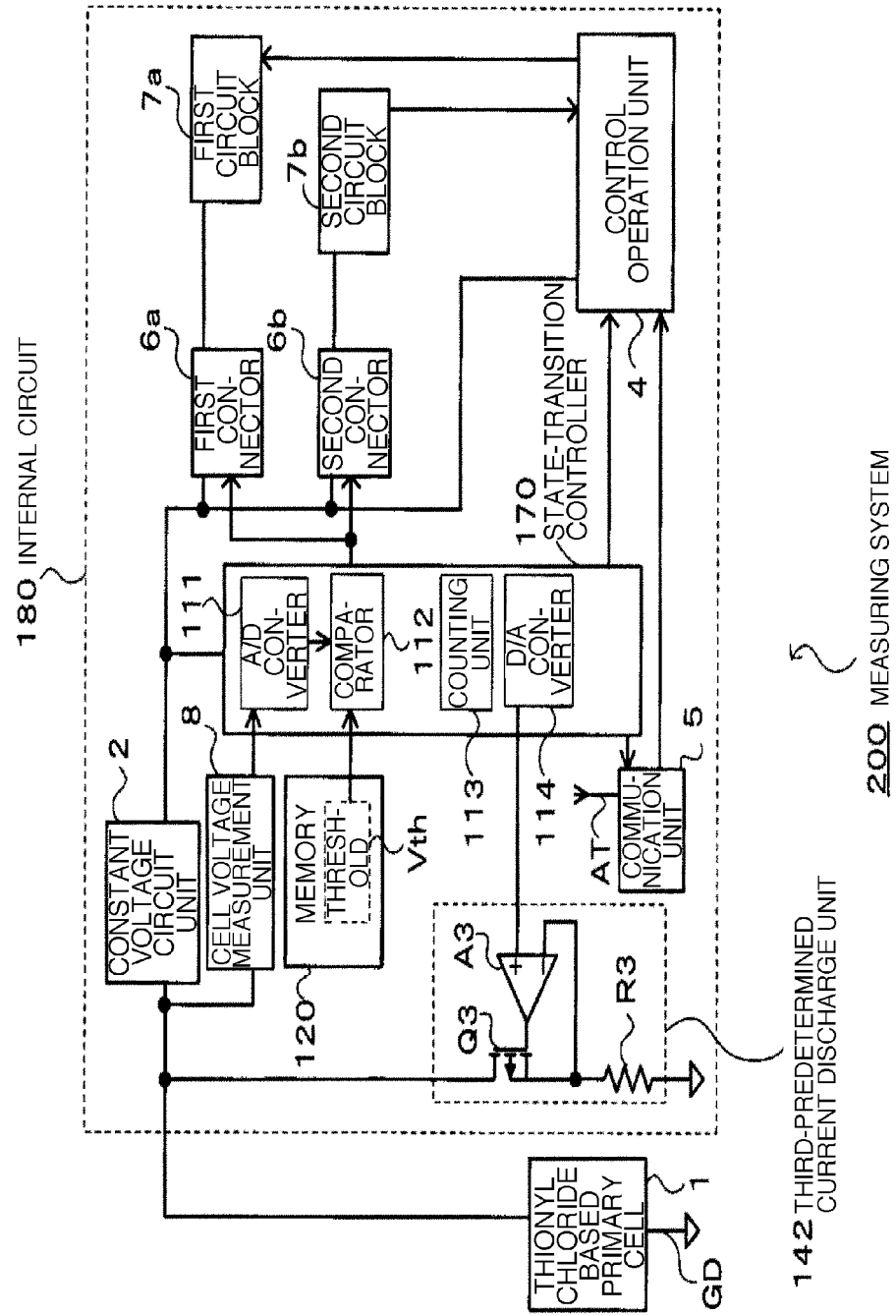
FIG. 5 is a block diagram of another embodiment of a measuring system according to the invention.

A second embodiment of a measuring system according to the invention is described with reference to FIG. 5. FIG. 5 is a block diagram of a measuring system 200 according to the invention.

In FIG. 5, the measuring system 200 comprises an internal circuit 180 wherein a third-predetermined current discharge unit 142 is provided in place of the first-predetermined current discharge unit 140, and the second-predetermined current discharge unit 141, shown in FIG. 1, the internal circuit 180 incorporating a state-transition controller 170 further comprising a D/A converter 114 as compared with the state-transition controller 110 in FIG. 1.

One of features of the measuring system 200 according to the invention lies in that a discharge current in the third-predetermined current discharge unit 142 can be altered by the third-predetermined current discharge unit 142, and the D/A converter 114, and explanation centering around the feature is described hereinafter. Further, in FIG. 5, constituents identical to those of the measuring system 160 shown in FIG. 1 are denoted by like reference numerals, omitting description thereof.

The third-predetermined current discharge unit 142 is provided with a resistance R3, a transistor (field effect transistor) Q3, and an operational amplifier A3.

The transistor Q3 has a drain connected to an anode (output) of a thionyl chloride based primary cell 1, a source connected to one end of the resistance R3, and a gate connected to an output of the operational amplifier A3. The resistance R3 has the other end connected to a common voltage GD of the circuit.

The operational amplifier A3 has an inverting input connected to a node between the source of the transistor Q3, and resistance R3, having a non-inverting input connected to an output of the D/A converter 114.

Now, there are described hereinafter operations of the third-predetermined current discharge unit 142, and the D/A converter 114, respectively. The third-predetermined current discharge unit 142 causes a current at a value obtained by dividing an analog voltage outputted from the D/A converter 114 by resistance R3 to flow as a predetermined discharge current.

A value of the predetermined discharge current flowing to the third-predetermined current discharge unit 142 can be altered by changing the analog voltage outputted from the D/A converter 114.

Thus, by changing the analog voltage outputted from the D/A converter 114, flow of a discharge current at a value optimal for removing or reducing a chloride can be realized, so that it is possible to normally execute the initial activation as well as the operation of the internal circuit 180, or prevent the internal circuit 180 from running away.

Furthermore, the state-transition controllers 110, 170 may be implemented by use of a processor for running a predetermined program, and so forth, or by use of a processor used in the control operation unit 4. The A/D converter 111, the comparator 112, the counting unit 113, and the D/A converter 114 may be installed separately from the state-transition controllers 110, 170, respectively.

The measuring systems 160, 200 each may be a system for measuring various measurement amounts besides the process parameters, such as electricity (voltage, electric current, electric power, and so forth), magnetism, sound, optical signals, and so forth.

Further, it is to be pointed out that the invention be not limited to the embodiments described in the foregoing, and that various changes and modification can be made in the invention without departing from the spirit and scope thereof. Furthermore, the invention can include a combination other than the combinations of the respective units as described in the foregoing.

What is claimed is:

1. A measuring system comprising:
   a thionyl chloride based primary cell,
   a predetermined current discharge unit for causing flow of a predetermined discharge current, and
   an internal circuit for receiving supply of a discharge current from the thionyl chloride based primary cell, having a plurality of states differing from each other in magnitude of the discharge current, said internal circuit comprising:
   a cell voltage measurement unit for taking measurements on an output voltage of the thionyl chloride based primary cell and providing a cell voltage measurement value,
   a unit for providing a threshold voltage value,
   a state-transition controller comprising a comparator for comparing the cell voltage measurement value to the threshold voltage value and providing an output to said predetermined current discharge unit,
   whereby said predetermined current discharge unit is operative in a discharge mode to permit a discharge current to flow from said thionyl chloride based primary cell and cause removal of any chloride film from said thionyl chloride based primary cell, and
   wherein in the case of transition of the internal circuit to a state thereof, having a discharge current larger than the discharge current in the present state thereof, the transition is made according to results of a comparison by said comparator of a voltage measured by the cell voltage measurement unit with a threshold on the basis of a discharge current in a state before, or after the transition of the internal circuit.

2. The measuring system according to claim 1, wherein the state-transition controller changes a value of the predetermined discharge current of the predetermined current discharge unit.

3. The measuring system according to claim 1, wherein if the state of the internal circuit, for flow of the predetermined discharge current by the action of the predetermined current discharge unit, is repeated a plurality of times, the state-transition controller prevents the internal circuit from making transition to another state of the internal circuit, where discharge current in another state is larger in value than discharge current in the present state of the internal circuit.

4. The measuring system according to claim 1, wherein if the voltage measured by the cell voltage measurement unit is smaller in value than the smallest threshold among the thresholds, the state-transition controller prevents the internal circuit from making transition to another state of the internal circuit, where discharge current in another state is larger in value than discharge current in the present state of the internal circuit.

5. A measuring system comprising:
a thionyl chloride based primary cell,
a cell voltage measurement unit for taking measurements on an output voltage of the thionyl chloride based primary cell, and
an internal circuit for receiving supply of a discharge current from the thionyl chloride based primary cell, having a plurality of states differing from each other in magnitude of the discharge current, said internal circuit comprising:

a state-transition controller wherein in the case of transition of the internal circuit to a state thereof, having a discharge current larger than the discharge current in the present state thereof, the transition is made according to results of comparison of a voltage measured by the cell voltage measurement unit with a threshold on the basis of a discharge current in a state before, or after the transition of the internal circuit,
wherein the threshold is a value based on a ratio of the discharge current in a state of the internal circuit, prior to transition, to the discharge current in a state of the internal circuit, after the transition, and based on a predetermined output voltage of the thionyl chloride based primary cell at no-load.

* * * * *